US005627285A

United States Patent [19]

Hanko et al.

[11] Patent Number: 5,627,285

[45] Date of Patent: May 6, 1997

[54] SULPHONYLBENZYL-SUBSTITUTED IMIDAZOLYLPROPENOIC ACID DERIVATIVES

[75] Inventors: Rudolf Hanko, Duesseldorf; Jürgen Dressel, Wuppertal; Peter Fey, Wuppertal; Walter Hübsch, Wuppertal; Thomas Krämer, Wuppertal; Ulrich E. Müller, Wuppertal; Matthias Müller-Gliemann, Solingen-Ohligs; Martin Beuck, Erkrath; Stanislav Kazda; Claudia Hirth-Dietrich, both of Wuppertal; Andreas Knorr, Erkrath; Johannes-Peter Stasch, Wuppertal; Stefan Wohlfeil, Hilden; Özkan Yalkinoglu, Wuppertal, all of Germany

[73] Assignee: Bayer Aktiengesellschaft, Leverkusen, Germany

[21] Appl. No.: 524,279

[22] Filed: Sep. 6, 1995

Related U.S. Application Data

[62] Division of Ser. No. 19,001, Feb. 18, 1993, Pat. No. 5,475,016.

[30] Foreign Application Priority Data

Feb. 27, 1992 [DE] Germany .......................... 42 06 041.9

[51] Int. Cl.$^6$ .................................................. C07D 403/12

[52] U.S. Cl. .......................................... 548/314.7; 548/111

[58] Field of Search .................................. 548/111, 314.7

[56] References Cited

U.S. PATENT DOCUMENTS 5,254,546 10/1993 Ardecky et al. ...................... 514/225.8

FOREIGN PATENT DOCUMENTS 0324377 7/1989 European Pat. Off. .
0403158 12/1990 European Pat. Off. .
0403159 12/1990 European Pat. Off. .
0425211 2/1991 European Pat. Off. .

OTHER PUBLICATIONS

Syst. No. 942, Funktionelle Derivate Der Hydrozimtasure p. 511 (1942).

*Primary Examiner*—Patricia L. Morris
*Attorney, Agent, or Firm*—Sprung Horn Kramer & Woods

[57] ABSTRACT

Sulphonylbenzyl-substituted imidazolylpropenoic acid derivatives can be prepared by reacting sulphonylbenzyl-substituted aldehydes with appropriate CH-acidic compounds and then dehydrating.

The sulphonylbenzyl-substituted imidazolylpropenoic acid derivatives can be used in medicaments, in particular for the treatment of high blood pressure and atherosclerosis.

3 Claims, No Drawings

SULPHONYLBENZYL-SUBSTITUTED IMIDAZOLYLPROPENOIC ACID DERIVATIVES

This application is a or divisional, of application Ser. No. 08/019,001, filed Feb. 18, 1993, now U.S. Pat. No. 5,475, 016.

The present invention relates to sulphonylbenzyl-substituted imidazolylpropenoic acid derivatives, to a process for their preparation and to their use in medicaments, in particular as hypotensive and anti-atherosclerotic agents.

It is known that renin, a proteolytic enzyme, cleaves the decapeptide angiotensin I in vivo from angiotensinogen, which is in turn degraded in the lungs, the kidneys or other tissues to give the hypertensive octapeptide angiotensin II. The various effects of angiotensin II, such as, for example, vasoconstriction, $Na^+$ retention in the kidney, aldosterone release in the adrenal gland and increase in tone of the sympathetic nervous system, act synergistically in the sense of a blood pressure increase.

Moreover, angiotensin II has the property of promoting the growth and the replication of cells such as, for example, of cardiac muscle cells and smooth muscle cells, these growing and proliferating in an increased manner in various disease states (for example hypertension, atherosclerosis and cardiac insufficiency).

In addition to the inhibition of renin activity, a possible starting point for intervention in the renin-angiotensin system (RAS) is the inhibition of the activity of angiotensin-converting enzyme (ACE) and the blockade of angiotensin II receptors.

The publications EP 324,377 A2, EP 403,158 A2 and EP 403,159 A2 describe phenyl (alkyl) imidazole- and imidazolylalkenoic acids.

The present invention relates to compounds of the general formula (I)

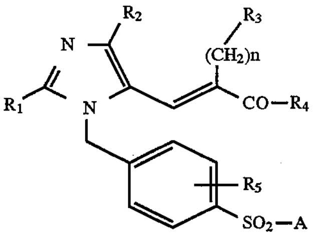

(I)

in which $R^1$ represents straight-chain or branched alkyl or alkenyl each having up to 8 carbon atoms, each of which is optionally substituted by cycloalkyl having 3 to 6 carbon atoms, or represents cycloalkyl having 3 to 8 carbon atoms, $R^2$ represents hydrogen, halogen or straight-chain or branched perfluoroalkyl having up to 8 carbon atoms, n represents a number 0, 1, 2, 3 or 4

$R^3$ represents hydrogen or represents straight-chain or branched alkyl having up to 8 carbon atoms, represents a 5- to 7-membered, saturated or unsaturated heterocycle having up to 2 further hereto atoms from the series consisting of S, N and O, or represents aryl having 6 to 10 carbon atoms, or represents cycloalkyl having 3 to 8 carbon atoms, where the cycles are optionally substituted up to 2 times by identical or different substituents from the group consisting of halogen, hydroxyl, nitro, cyano, trifluoromethyl and trifluoromethoxy or by straight-chain or branched alkyl or alkoxy each having up to 8 carbon atoms, $R^4$ represents hydroxyl, straight-chain or branched alkoxy having up to 8 carbon atoms, phenoxy or a group of the formula $—NR^6R^7$ in which $R^6$ and $R^7$ are identical or different and denote hydrogen or straight-chain or branched alkyl having up to 6 carbon atoms or phenyl, $R^5$ represents hydrogen, halogen or straight-chain or branched alkyl having up to 8 carbon atoms, or represents straight-chain or branched perfluoroalkyl having up to 6 carbon atoms, or represents a group of the formula —OX, in which X denotes hydrogen, benzyl, a hydroxyl protective group or denotes straight-chain or branched alkyl having up to 8 carbon atoms A represents a 3- to 8-membered, saturated heterocycle bonded via the nitrogen atom and having up to 2 further hetero atoms from the series consisting of S, N and O and which is optionally substituted up to 2 times by identical or different perfluoroalkyl having up to 5 carbon atoms or by a radical of the formula $—SO_3H$, 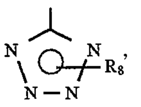 , $—CO—R^9$ or $—P(O)(OR^{10})(OR^{11})$ in which $R^8$ denotes hydrogen, straight-chain or branched alkyl having up to 6 carbon atoms or triphenylmethyl $R^9$ has the abovementioned meaning of $R^4$ and is identical to or different from this and $R^{10}$ and $R^{11}$ are identical or different and denote hydrogen, straight-chain or branched alkyl having up to 8 carbon atoms or phenyl, and their salts.

The sulphonylbenzyl-substituted imidazolylpropenoic acid derivatives according to the invention can also be present in the form of their salts. In general, salts with organic or inorganic bases or acids may be mentioned here.

In the context of the present invention, physiologically acceptable salts are preferred. Physiologically acceptable salts of the sulphonylbenzyl-substituted imidazolylpropenoic acid derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and also ammonium salts which are derived from ammonia or organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms, either as enantiomers or as diastereomers. The invention relates both to the enantiomers or diastereomers and their respective mixtures. The racemic forms, like the diastereomers, can be separated in a known manner into the stereoisomerically uniform constituents [cf. E. L. Eliel, Stereochemistry of Carbon Compounds, McGraw Hill, 1962].

Preferred compounds of the general formula (I) are those in which $R^1$ represents straight-chain or branched alkyl or alkenyl each having up to 6 carbon atoms, each of which is optionally substituted by cyclopropyl, cyclobutyl, cyclopentyl or cyclohexyl, represents cyclopropyl, cyclopentyl or cyclohexyl, $R^2$ represents hydrogen, fluorine, chlorine, bromine or straight-chain or branched perfluoroalkyl having up to 6 carbon atoms, n represents a number 0, 1, 2 or 3

$R^3$ represents hydrogen or represents straight-chain or branched alkyl having up to 6 carbon atoms, represents thienyl, phenyl, cyclopropyl, cyclopentyl, cyclohexyl or cycloheptyl, which are optionally substituted up to 2 times by identical or different substituents from the group consisting of fluorine, chlorine, bromine, hydroxyl, nitro, cyano, trifluoromethyl and trifluoromethoxy or by straight-chain or branched alkyl or alkoky each having up to 6 carbon atoms, $R^4$ represents hydroxyl, straight-chain or branched alkoxy having up to 6 carbon atoms, phenoxy or a group of the formula $-NR^6R^7$, in which $R^6$ and $R^7$ are identical or different and denote hydrogen or straight-chain or branched alkyl having up to 4 carbon atoms, $R^5$ represents hydrogen, fluorine, chlorine, bromine, straight-chain or branched alkyl having up to 6 carbon atoms, or represents straight-chain or branched perfluoroalkyl having up to 4 carbon atoms, or represents a group of the formula —OX, in which X denotes hydrogen, benzyl, acetyl or straight-chain or branched alkyl with up to 6 cubon morns A represents piperidyl, pyrrolidinyl or morpholinyl bonded via the nitrogen atom, which are optionally substituted by trifluoromethyl or by a radical of the formula $-SO_3H$, 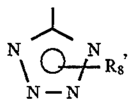, $-CO-R^9$ or 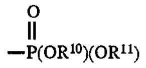

in which $R^8$ denotes hydrogen, straight-chain or branched alkyl having up to 4 carbon atoms or triphenylmethyl $R^9$ has the abovementioned meaning of $R^4$ and is identical to or different from this and $R^{10}$ and $R^{11}$ are identical or different and denote hydrogen or straight-chain or branched alkyl having up to 6 carbon atoms or phenyl, and their salts.

In addition, a process for the preparation of the compounds of the general formula (I) according to the invention has been found, characterised in that aldehydes of the general formula (II)

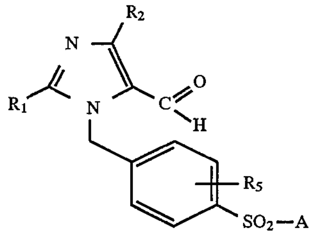

(II)

in which $R^1$, $R^2$, $R^5$ and A have the abovementioned meaning, are first converted by reaction with CH-acidic compounds of the general formula (III)

$$R^3-(CH_2)_n-CH_2-CO_2-R^{12} \quad (III)$$

in which $R^3$ and n have the abovementioned meaning and $R^{12}$ has the abovementioned meaning of $R^4$, but does not represent hydrogen, in inert solvents, in the presence of a base, to give the compounds of the general formula (IV)

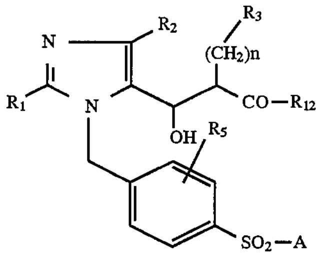

(IV)

in which $R^1$, $R^2$, $R^3$, $R^5$, $R^{12}$ and A have the abovementioned meaning, then the free hydroxyl function is blocked by introduction of a protective group and in a last step an elimination in inert solvents in the presence of a base is carried out, and in the case of the acids ($R^4$=OH) the esters are hydrolysed and in the case in which $R^8$ does not represent hydrogen, the —NH function is alkylated.

The process according to the invention can be illustrated by way of example by the following reaction scheme:

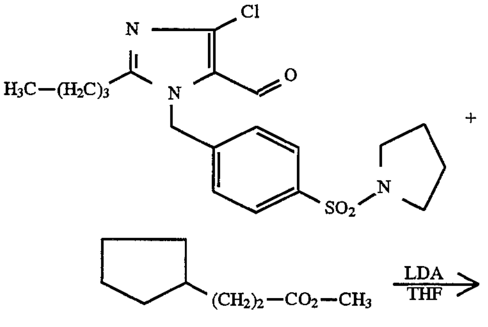

-continued

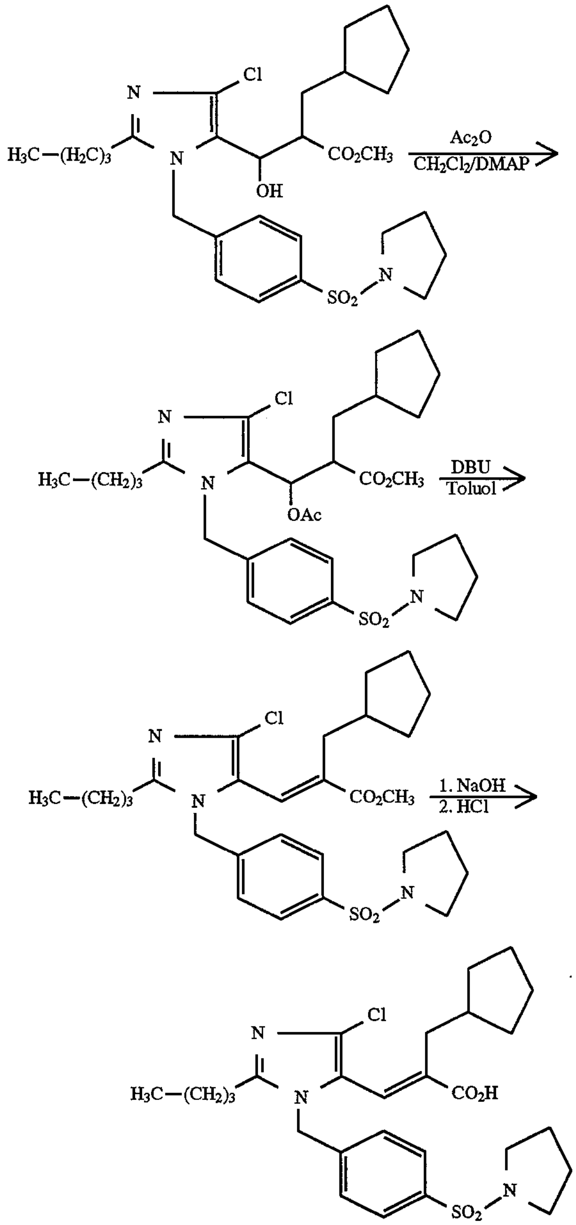

Hydroxyl protective group in the context of the abovementioned definition in general represents a protective group from the series comprising: benzyloxycarbonyl, methanesulphonyl, toluenesulphonyl, 2-nitrobenzyl, 4-nitrobenzyl, 2-nitrobenzyloxycarbonyl, 4-nitrobenzyloxycarbonyl, tert-butoxycarbonyl, allyloxycarbonyl, 4-methoxycarbonyl, acetyl, trichloroacetyl, 2,2,2-trichloroethoxycarbonyl, 2,4-dimethoxybenzyloxycarbonyl, 2-(methylthiomethoxy) ethoxycarbonyl, benzoyl, 4-methylbenzoyl, 4-nitrobenzoyl, 4-fluorobenzoyl, 4-chlorobenzoyl or 4-methoxybenzoyl. Acetyl, methanesulphonyl and toluenesulphonyl are preferred.

Suitable solvents for the process are the customary organic solvents which do not change under the-reaction conditions. These preferably include ethers such as diethyl ether, dioxane, tetrahydrofuran, glycol dimethyl ether, and hydrocarbons such as benzene, toluene, xylene, hexane, cyclohexane or mineral oil fractions, and halogenohydrocarbons such as dichloromethane, trichloromethane, tetrachloromethane, dichloroethylene, trichloroethylene or chlorobenzene, and ethyl acetate, triethylamine, pyridine, dimethyl sulphoxide, dimethylformamide, hexamethylphosphoric triamide, acetonitrile, acetone and nitromethane. It is also possible to use mixtures of the solvents mentioned. Tetrahydrofuran, methylene chloride and toluene are preferred for the various steps.

Bases which can be employed for the process according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, and alkali metal or alkaline earth metal alkoxides or amides such as sodium methoxide or potassium methoxide, sodium ethoxide or potassium ethoxide or potassium tert-butoxide or lithium diisopropylamide (LDA), and organic amines (trialkyl-($C_1$–$C_6$)amines) such as triethylamine or N,N-diisopropylamine, and heterocycles such as 1,4-diazabicyclo[2.2.2]-octane (DABCO), 1,8-diazabicyclo[5.4.0]undec-7-ene (DBU), pyridine, diaminopyridine, methylpiperidine or morpholine. It is also possible to employ as bases alkali metals, such as sodium, or their hydrides such as sodium hydride. Sodium hydride, lithium diisopropylamide (LDA), DBU and N,N-diisopropylamine are preferred.

In general, the base is employed in an amount from 0.05 mol to 10 mol, preferably from 1 mol to 2 mol, relative to 1 mol of the compound of the formula (III).

The process according to the invention is in general carried out in a temperature range from −100° C. to +100° C., preferably at −78° C.

The process according to the invention is in general carried out at normal pressure. However, it is also possible to carry out the process at elevated pressure or at reduced pressure (for example in a range from 0.5 to 5 bar).

The introduction of the protective group is in general, carried out in one of the abovementioned solvents and a base, preferably in methylene chloride using dimethylaminopyridine.

The blocking is in general carried out in a temperature range from 0° C. to +60° C., preferably at room temperature and at normal pressure.

The elimination is in general carried out in one of the abovementioned solvents, preferably in toluene and in the presence of one of the bases mentioned, preferably DBU.

The elimination is in general carried out in a temperature range from +30° C. to +130° C., preferably at +50° C. to +100° C. and at normal pressure.

Suitable bases for the hydrolysis are the customary inorganic bases. These preferably include alkali metal hydroxides and alkaline earth metal hydroxides such as, for example, sodium hydroxide, potassium hydroxide or barium hydroxide, and alkali metal carbonates such as sodium carbonate or potassium carbonate or sodium hydrogen carbonate and alkali metal alkoxides such as sodium methoxide, sodium ethoxide, potassium methoxide, potassium ethoxide or potassium tert-butoxide. Sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, and ethers such as tetrahydrofuran or dioxane, and dimethylformamide, and dimethyl sulphoxide. Particularly preferably, alcohols such as methanol, ethanol, propanol or isopropanol are used. It is also possible to employ mixtures of the solvents mentioned.

The hydrolysis can also be carried out using acids such as, for example, trifluoroacetic acid, acetic acid, hydrochloric acid, hydrobromic acid, methanesulphonic acid, sulphuric acid or perchloric acid, preferably using trifluoroacetic acid.

The hydrolysis is in general carried out in a temperature range from 0° C. to +100° C. preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Particularly preferably, molar amounts of the reactants are used.

When carrying out the reaction, in the first step the carboxylates of the compounds according to the invention are formed as intermediates which can be isolated. The acids according to the invention are obtained by treating, the carboxylates with customary inorganic acids. These preferably include mineral acids such as, for example, hydrochloric acid, hydrobromic acid, sulphuric acid or phosphoric acid. It has proved advantageous in the preparation of the carboxylic acids in this connection to acidify the basic reaction mixture from the hydrolysis in a second step without isolation of the carboxylates. The acids can then be isolated in a customary manner. In the case of the basic heterocycles, by treatment of the solutions of the carboxylates with the abovementioned acids the salts of the heterocycles with the inorganic acids can also be obtained.

The alkylation is in general carried out using alkylating agents such as, for example, $(C_1-C_6)$-alkyl halides, sulphonic acid esters or substituted or unsubstituted $(C_1-C_6)$-dialkyl or $(C_1-C_6)$-diaryl sulphates, preferably methyl iodide or dimethyl sulphate.

The alkylation is in general carried out in one of the abovementioned solvents, preferably in dimethylformamide, in a temperature range from 0° C. to +70° C., preferably from 0° C. to +30° C. and at normal pressure.

The aldehydes of the general formula (II) are also new and can be prepared by reacting imidazoles of the general formula (V)

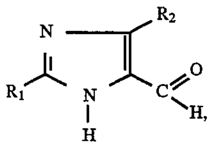

(V)

in which $R^1$ and $R^2$ have the abovementioned meaning, with compounds of the general formula (VI)

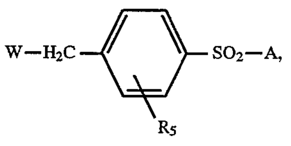

(VI)

in which $R^5$ and A have the abovementioned meaning and

W represents halogen, preferably bromine, in one of the abovementioned solvents in the presence of one of the bases mentioned there, preferably in dimethylformamide, using sodium hydride.

The compounds of the general formula (VI) are new and can be prepared by reacting substituted benzylsulphonyl chlorides of the general formula (VII)

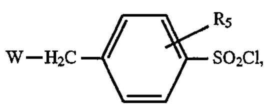

(VII)

in which

W and $R^5$ have the abovementioned meaning with compounds of the general formula (VIII)

H-A (VIII), in which

A has the abovementioned meaning, in one of the abovementioned solvents and bases, preferably in dichloromethane, using triethylamine, The reaction is in general carried out in a temperature range from 0° C. to +100° C., preferably from +20° C. to +80° C.

In general, the reaction is carried out at normal pressure. However, it is also possible to work at reduced pressure or at elevated pressure (for example from 0.5 to 5 bar).

When carrying out the reaction, the base is in general employed in an amount from 1 to 3 mol, preferably from 1 to 1.5 mol, relative to 1 mol of the compounds of the general formulae (V) and (VII). Molar amounts of the reactants are particularly preferably used.

The reaction is in general carried out in a temperature range from −10° C. to +40° C., preferably from −10° C. to 0° C., and under normal pressure.

The compounds of the general formulae (VII) and (VIII) are known or can be prepared by a customary method.

The CH-acidic compounds of the general formula (III) are known or can be prepared by a customary method [cf., for example, Beilstein 9,511].

The compounds of the general formula (IV) are also new and can be prepared by the abovementioned process.

The compounds of the general formula (I) according to the invention exhibit an unforeseeable, useful pharmacological spectrum of action.

The compounds according to the invention have a specific A II-antagonistic action, since they competitively inhibit the binding of angiotensin II to A II receptors. They suppress the vasoconstrictory and aldosterone secretion-stimulating effects of angiotensin II. Moreover, they inhibit the proliferation of smooth muscle cells.

They can therefore be employed in medicaments for the treatment of arterial hypertension and atherosclerosis. Moreover, they can be used for the treatment of coronary heart diseases, cardiac insufficiency, disorders of cerebral function, ischaemic brain disorders, peripheral circulatorydisorders, functional disorders of the kidney and adrenal gland, bronchospastic and vascularly conditioned disorders of the airways, sodium retention and oedemas.

Moreover, the substances have natriuretic and diuretic action. This action is manifested in a mobilisation of oedema fluid with an increase in pathological fluid of cardiac and non-cardiac origin.

Investigation of the Inhibition of the Contraction Induced with Agonists

Rabbits of both sexes are anaesthetised by a blow to the neck and bled out, or alternatively anaesthetised with Nembutal (about 60–80 mg/kg i.v.) and sacrificed by opening the thorax. The thorax aorta is taken out, freed from adhering connective tissue, divided into 1.5 mm-wide ring segments and these are individually transferred under an initial loading of about 3.5 g to 10-ml organ baths containing 95%

$O_2$/5% $CO_2$-aerated Krebs-Henseleit nutrient solution, thermostated at 37° C., of the following composition: 119 mmol/l NaCl; 2.5 mmol/l $CaCl_2 \times 2H_2O$; 1.2 mmol/l $KH_2PO_4$; 10 mmol/l glucose; 4.8 mmol/l KCl; 1.4 mmol/l $MgSO_4 \times 7\ H_2O$ and 25 mmol/l $NaHCO_3$.

The contractions are detected isometrically by Statham UC2 cells by means of a bridge amplifier (ifd Mülheim or DSM Aalen) and digitised and evaluated by means of an A/D converter (System 570, Keithley, Munich). The implementation of agonist dose-response curves (DRC) is carried out hourly. With each DRC, 3 or 4 individual concentrations are applied to the baths at 4-min intervals. After the end of the DRC and subsequent washing-out cycles (16 times, in each case about 5 sec/min with the abovementioned nutrient solution), a 28-minute rest or incubation phase follows, in the course of which the contractions as a rule reach the starting value again.

The height of, in the normal case, the 3rd DRC is used as a reference quantity for the assessment of the test substance to be investigated in further runs, which test substance in the following DRCs is applied at the start of the incubation time to the baths, in each case in an increasing dose. Each aorta ring is in this case stimulated for the whole day, always with the same agohist.

| Agonists and their standard concentrations (administration volume per individual dose = 100 μl); | | |
|---|---|---|
| KCl | 22.7; 32.7; 42.7; 52.7 | mmol/l |
| 1-Noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$ | g/ml |
| Methoxamine | $10^{-7}$; $10^{-6}$; $10^{-5}$ | g/ml |
| Angiotensin II | $3 \times 10^{-9}$; $10^{-8}$; $3 \times 10^{-8}$; $10^{-7}$ | g/ml |

For the calculation of the $IC_{50}$ (concentration at which the substance to be investigated causes a 50% inhibition), the effect in each case at the 3rd=submaximal agonist concentration is used as a basis.

The compounds according to the invention inhibit the contraction of the isolated rabbit aorta induced by angiotensin II in a dose-dependent manner. The contraction induced by potassium depolarisation or other agonists was not inhibited, or only weakly inhibited at high concentrations.

TABLE A

Inhibition of the vascular contraction in isolated aorta rings of rabbits in vitro $IC_{50}$ [nM] against contractions induced by:

| Ex. No.: | AII $IC_{50}$ [nM] |
|---|---|
| 19 | 40 |
| 2 | 11 |
| 39 | 4 |
| 55 | 3 |
| 24 | 1 |
| 43 | 3 |
| 47 | 4 |
| 53 | 6 |
| 57 | 6 |

Blood Pressure Measurements on the Angiotensin II-Infused Rat

Male Wistar rats (Moellegaard, Copenhagen, Denmark) having a body weight of 300–350 g are anaesthetised with thiopental (100 mg/kg i.p.). After tracheotomy, a catheter is inserted in the femoral artery for blood pressure measurement and a catheter for angiotensin II infusion and a catheter for substance administration are inserted in the femoral veins. After administration of the ganglionic blocker pentolinium (5 mg/kg i.v.), the angiotensin II infusion (0.3 μg/kg/min) is started. As soon as the blood pressure values have reached a stable plateau, the test substances are administered either, intravenously or orally as a suspension or solution in 0.5% Tylose. The blood pressure changes under the influence of substance are indicated in the table as average values ±SEM.

TABLE B

| Ex. No.: | mg/kg p.o. | Blood Pressure measurement |
|---|---|---|
| 23 | 0.1 | −17 mm HG |
| 24 | | |
| 43 | 0.1 | −10 mm Hg |
| 47 | | |
| 41 | 0.1 | −11 mm Hg |
| 53 | | |
| 57 | | |

Determination of the Antihypertensive Activity in Conscious Hypertensive Rats

The oral antihypertensive activity of the compounds according to the invention was tested on conscious rats having surgically induced unilateral renal artery stenosis. For this, the right renal artery was constricted with a silver clip of 0.18-mm internal width. In this form of hypertension, the plasma renin activity is increased in the first six weeks after intervention. The arterial blood pressure of these animals was measured by bloodless means at defined time intervals after substance administration using the "tail cuff". The substances to be tested were administered intragastrally ("orally") by stomach tube in different doses, suspended in a Tylose suspension. The compounds according to the invention lower the arterial blood pressure of the hypertensive rats at a clinically relevant dosage.

In addition, the compounds according to the invention inhibit the specific binding of radioactive angiotensin II in a concentration-dependent manner.

Interaction of the Compounds According to the Invention with the Angiotensin II Receptor on Membrane Fractions of the Adrenal Gland Cortex (Cattle)

Adrenal gland cortices of cattle (AGC), which have been freshly removed and carefully freed from gland medulla, are comminuted in sucrose solution (0.32M) with the aid of an Ultra-Turrax (Janke & Kunkel, Staufen i.B.) to give a coarse membrane homogenate and are partially purified in two centrifugation steps to give membrane fractions. The receptor binding investigations are carried out on partially purified membrane fractions of bovine AGC using radioactive angiotensin II in an assay volume of 0.25 ml, which in detail contains the partially purified membranes (50–80 μg), $^3H$-angiotensin II (3–5 nM), test buffer solution (50 mM tris, pH 7.2, 5 mM $MgCl_2$, 0.25% BSA) and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM tris/HCl, pH 7.4, 5% PEG 6000). The analysis of the raw data was carried out using computer programs to give $K_i$ or $IC_{50}$ values ($K_i$: $IC_{50}$ values corrected for the radioactivity used; $IC_{50}$ values: concentration at which the substance to be investigated causes a 50% inhibition of the specific binding of the radioligand).

Ex. 9 Ki=100 nM
Ex. 10 Ki=40 nM
Ex. 20 Ki=40 nM
Ex. 30 Ki=120 nM

Investigation of Inhibition of the Proliferation of Smooth Muscle Cells by the Compounds According to the Invention To determine the antiproliferative action of the compounds, smooth muscle cells are used which have been obtained from the aortas of rats or pigs by the media explant technique [R. Ross, J. Cell. Biol. 50, 172, 1971]. The cells are inoculated into suitable culture dishes, as a rule 24-hole plates, and cultured at 37° C. in 5% $CO_2$ for 2–3 days in Medium 199 containing 7.5% FCS and 7.5% NCS, 2 mM L-glutamine and 15 mM HEPES, pH 7.4. After this, the cells are synchronised by withdrawal of serum for 2–3 days and then stimulated into growth with AII, serum or other factors. At the same time, test compounds are added. After 16–20 hours, 1 μCi of $^3$H-thymidine is added and the incorporation of this substance into the TCA-precipitable DNA of the cells is determined after a further 4 hours.

| Example No. | % inihibition at $10^{-6}$ M |
|---|---|
| 6 | 70 |
| 7 | 30 |

Test for Naurrivretic Effect

Fasting Wistar rats are treated orally with test substance (suspended in Tylose solution). The urine excretion is then collected in diuresis cages over the course of 6 hours. The concentration of sodium and potassium in the urine is determined by flame photometry.

The new active substance can be converted in a known manner into the customary formulations, such as tablets, coated tablets, pills, granules, aerosols, syrups, emulsions, suspensions and solutions, using inert, nontoxic, pharmaceutically suitable excipients or solvents. The therapeutically active compound should in each case be present in a concentration of about 0.5 to 90% by weight of the total mixture, i.e. in amounts which are sufficient in order to achieve the dosage range indicated.

The formulations are prepared, for example, by extending the active substances with solvents and/or excipients, if appropriate using emulsifiers and/or dispersants, where, for example, in the case of the use of water as a diluent, organic solvents can be used as auxiliary solvents if appropriate.

Administration is carried out in a customary manner, preferably orally or parenterally, in particular per-lingually or intravenously.

In the case of parenteral administration, solutions of the active substance using suitable liquid excipients can be employed.

In general, it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg of body weight.

In spite of this, it may be necessary to depart from the amounts mentioned, in particular depending on the body weight or the type of administration route, on individual behaviour towards the medicament, the manner of its formulation and the time or interval at which administration takes place. Thus, in some cases, it may be sufficient to manage with less than the abovementioned minimum amount, while in other cases the upper limit mentioned must be exceeded. In the case of the administration of larger amounts, it may be advisable to divide these into several individual doses over the course of the day.

Mobile phase mixtures:

a=methylene chloride/methanol 20:1
b=methylene chloride/methanol 10:1
c=methylene chloride/ethyl acetate 15:1
d=methylene chloride/ethyl acetate 10:1
e=methylene chloride/ethyl acetate 30:1
f=toluene/ethyl acetate/acetic acid=20:20:1

Starting Compounds

EXAMPLE I 4-(Bromomethyl)bnzene-sulphochloride

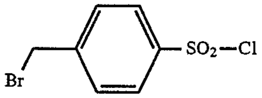

38.1 g (0.2 mol) of 4-methylbenzenesulphonyl chloride are dissolved in 300 ml of carbon tetrachloride and treated with 35.6 g (0.2 mol) of N-bromosuccinimide and, after addition of 0.2 g (1.2 mmol) of azobisisobutyronitrile (ABU), the mixture is heated under reflux for 4 h. After cooling, the solids are filtered off and the filtrate is freed from the solvent. Flash chromatography (petroleum ether/toluene 4:1, 50 μm particle size) and subsequent recrystallisation from 100 ml of cyclohexane gives 24.0 g (45% of theory) of the title compound. $R_f$=0.75 (toluene)

EXAMPLE II 4-(Bromomethyl)-3-chlorobenzenesulphochloride

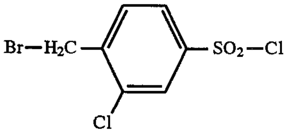

45.9 g (0.2 mol) of sodium 3-chloro-4-methylbenzenesulphonate are mixed with 83.3 g (0.4 mol) of phosphorus pentachloride and heated for 30 min at an oil bath temperature of 140° C. The hot mixture is treated with 500 ml of toluene, and the resulting solution is heated to boiling and, after cooling, poured onto ice. The organic phase is separated off and washed with water (2×200 ml). After drying over $MgSO_4$, it is filtered and all the volatiles are stripped off in vacuo. The residue obtained is purified by flash chromatography (petroleum ether/toluene 4:1, 50 μm particle size). 24.9 g of a product are obtained which is immediately reacted further:

It is taken up in 200 ml of carbon tetrachloride and, after addition of 19.6 g (0.11 mol) of N-bromosuccinimide and 0.1 g (0.6 mmol) of ABN, heated under reflux for 6 h. After cooling, the solids are filtered off and the filtrate is freed from solvent. Flash chromatography (petroleum ether/toluene 4:1, 50 μm particle size) gives 21.2 g (35%) of the title compound. $R_f$=0.32 (petroleum ether/dichloromethane 4:1)

EXAMPLE III 5 4-(Bromomethyl)-benzenesulphonyl-N-pyrrolidinide

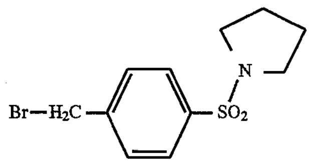

5.3 g (0.02 mol) of the compound from Example III are dissolved in 200 ml of dichloromethane and 4.0 g (0.04 mol) of triethylamine and, after addition of 1.4 g (0.02 mol) of pyrrolidine, the mixture is stirred at 0° C. for 1 h in 50 ml of dichloromethane. The mixture is extracted with 2N HCl (2×100 ml), $H_2O$ (2×100 ml), dried over $MgSO_4$ and filtered, and all the volatile components are evaporated in vacuo.

Yield: 5.4 g (89% of theory)

$R_f$=0.09 (toluene)

EXAMPLE IV 4-(Bromomethyl)-benzenesulphonyl-N-piperidinide

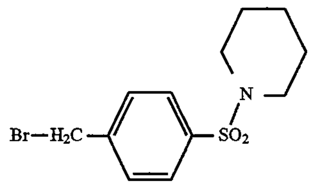

In analogy to the procedure of Example III, 1.0 g (81% of theory) of the title compound is obtained from 1.1 g (4 mmol) of the compound from Example III and 0.34 g (4 mmol) of piperidine.

$R_f$=0.14 (toluene)

EXAMPLE V (S)-4-(Bromomethyl)-benzenesulphonyl-N-2-(tert-butoxycarbonyl)pyrrolidinide

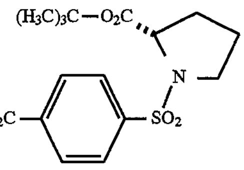

In analogy to the procedure of Example III, 9.1 g (84% of theory) of the title compound are obtained from 7.25 g (27 mmol) of the compound from Example III and 4.6 g (27 mmol) of S-proline tert-butyl ester.

Rf=0.66 (petroleum ether/ethyl acetate 7:3)

EXAMPLE VI rac-4-(Bromomethyl)-benzenesulphonyl-N-2-(tert-butoxycarbonyl)piperidinide

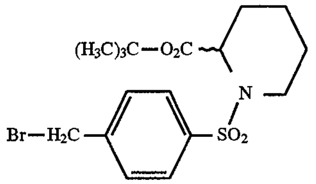

In analogy to the procedure of Example III, 7.4 g (59% of theory) of the title compound are obtained from 8.0 g (30 mmol) of the compound from Example III and 5.5 g (30 mmol) of tert-butyl rac-pipecolate.

$R_f$=0.53 (petroleum ether/ethyl acetate 5:1)

EXAMPLE VII (S)-4-(Bromomethyl)-3-chlorobenzenesulphonyl-N-2-(tertbutoxycarbonyl)pyrrolidinide

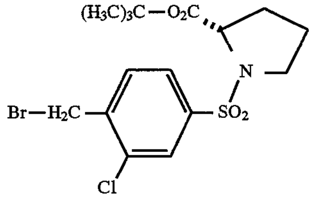

In analogy to the procedure of Example III, 13.9 g (96% of theory) of the title compound are obtained from 10.0 g (33 mmol) of the compound from Example IV and 5.7 g (33 mmol) of S-proline tert-butyl ester.

$R_f$=0.55 (petroleum ether/ethyl acetate 7:3)

EXAMPLE VIII rac-4-(Bromomethyl)-3-chlorobenzenesulphonyl-N-2-(tertbutoxycarbonyl)piperidinide

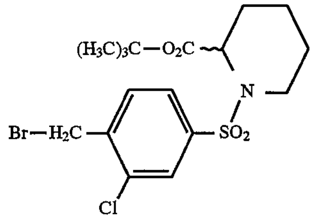

In analogy to the procedure of Example III, 14.6 g (98% of theory) of the title compound are obtained from 10.0 g (33 mmol) of the compound from Example IV and 6.1 g (33 mmol) of tert-butyl rac-pipecolate.

$R_f$=0.6 (petroleum ether/ethyl acetate 7:3)

EXAMPLE IX

4-[(2-Butyl-4-chloro-5-formylimidazolyl)methyl] benzenesulphonyl-N-pyrrolidinide

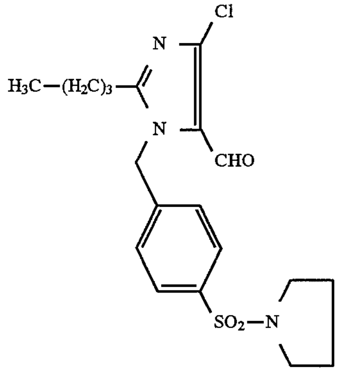

1.1 g (6.0 mmol) of 2-butyl-4-chloro-5-formylimidazole are treated in 12 ml of dimethylformamide with 180 mg (6.0 mmol) of an 80% strength dispersion of sodium hydride in mineral oil and the mixture is stirred at 20° C. for 30 min. It is cooled to 0° C. and 1.8 g (6.0 mmol) of the compound from Example III in 15 ml of DMF are added. The mixture is stirred at 20° C. for 2.5 h and the reaction mixture is poured onto ice and extracted with ethyl acetate (3×50 ml), and the combined organic phases are washed with saturated sodium chloride solution (5×50 ml), dried over $MgSO_4$ and filtered, and all the volatiles are stripped off in vacuo. The crude product is purified by flash chromotography (petroleum ether/ethyl acetate 10:1→3:1, 50 μm particle size), and 1.1 g (60% of theory) of the title compound are obtained.

$R_f$=0.14 (toluene)

EXAMPLE X

4-[(2-Butyl-4-chloro-5-formylimidazolyl)methyl] benzenesulphonyl-N-piperidinide

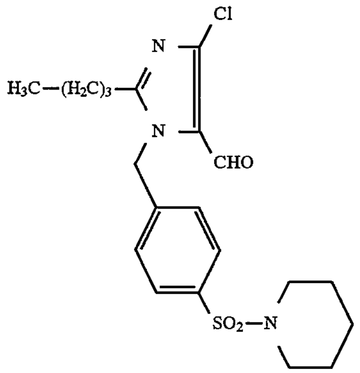

In anslogy to the procedure of Example IX, 3.1 g (61% of theory) of the title compound are obtained from 3.8 g (12.0 mmol) of the compound from Example III and 2.2 g of 2-butyl-4-chloro-5-formylimidazole.

$R_f$=0.39 (petroleum ether/ethyl acetate 7:3)

EXAMPLE XI (S)-4-[(2-Butyl-4-chloro-5-formylimidazolyl) methyl]-benzenesulphonyl-N-(2-tert-butoxycarbonyl)pyrrolidinide

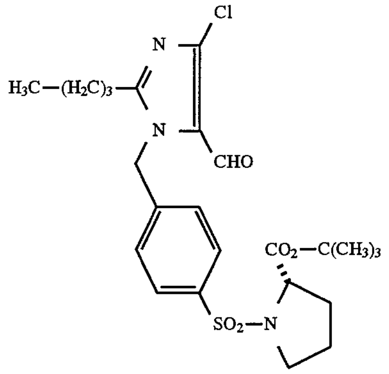

In analogy to the procedure of Example IX, 6.0 g (74% of theory) of the title compound are obtained from 9.1 g (23 mmol) of the compound from Example V and 3.0 g (16 mmol) of 2-butyl-4-chloro-5-formylimidazole.

$R_f$=0.61 (petroleum ether/ethyl acetate 7:3)

EXAMPLE XII rac-4-[(2-Butyl-4-chloro-5-formylimidazolyl) methyl]-benzenesulphonyl-N-(2-tert-butoxycarbonyl)piperidinide

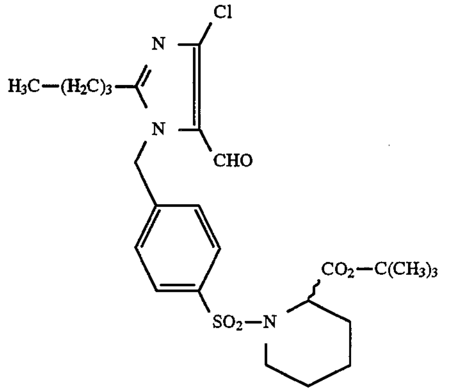

In analogy to the procedure of Example IX, 4.9 g (53% of theory) of the title compound are obtained from 7.4 g (18 mmol) of the compound from Example VI and 3.3 g (18 mmol) of 2-butyl-4-chloro-5-formylimidazole .

$R_f$=0.08 (petroleum ether/ethyl acetate 7:1)

EXAMPLE XIII (S)-4-[(2-Butyl-4-chloro-5-formylimidazolyl)methyl]-3-chlorobenzenesulphonyl-N-(2-tert-butoxycarbonyl)pyrrolidinide

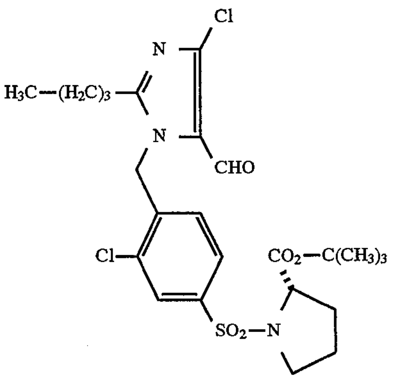

In analogy to the procedure of Example IX, 2.7 g (42% theory) of the title compound are obtained from 6.6 g (15 mmol) of the compound from Example VII and 2.2 g (12 mmol) of 2-butyl-4-chloro-5-formylimidazole.

$R_f$=0.75 (dichloromethane/ethylacetate 10:1)

EXAMPLE XIV rac-4-[(2-Butyl-4-chloro-5-formylimidazolyl)methyl]-3-chlorobenzenesulphonyl-N-(2-tert-butoxycarbonyl)piperidinide

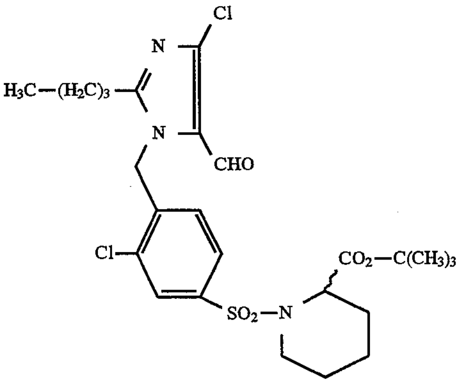

In analogy to the procedure of Example IX, 2.4 g (26% of theory) of the title compound are obtained from 6.8 g (15 mmol) of the compound from Example VIII and 2.2 g (12 mmol) of 2-butyl-4-chloro-5-formylimidazole.

$R_f$=0.87 (dichloromethane/ethylacetate 10:1)

EXAMPLE XV (S)-4-[(2-Butyl-5-formylimidazolyl)methyl]-3-chloro-benzenesulphonyl-N-(2-tert-butoxycarbonyl)pyrrolidinide

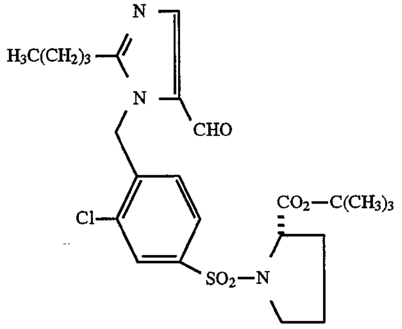

4.98 g (9.15 mmol) of the compound from Example XIII are dissolved in 100 ml of THF/50 ml of methanol and the solution is hydrogenated at a hydrogen pressure of about 3 bar for 1 h in the presence of 1.24 g (9.15 mmol) of sodium acetate trihydrate and 0.5 g of palladium on active carbon (5% strength). The solution is then filtered off from the catalyst and concentrated, and the residue is purified on silica gel using ethyl acetate/petroleum ether (1:1 and 2:1).

Yield: 3.3 g (71% of theory).

$R_f$: 0.18 (ethyl<acetate/petroleum ether=1:1).

EXAMPLE XVI

N-Trifluoroacetyl-L-prolinamide

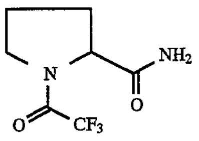

30 g (0.142 mol) of trifluoroacetylproline are initially introduced into 150 ml of DMF under protective gas. At −20° C., 142.6 ml (0.1704 mol) of 38% strength PPA in ethyl acetate are added. Ammonia is introduced until the mixture is saturated, a white precipitate depositing after 30 min. The batch is thawed under a gentle stream of ammonia. The whole reaction mixture is then added to 600 ml of $H_2O$ and acidified to pH 4 with concentrated acetic acid. It is extracted 4× by shaking with 200 ml of methylene chloride and 3× by shaking with 200 ml of ether. The combined organic phases are dried using magnesium sulphate and the solvent is stripped off. The residues are chromatographed together on silica gel 60 F254 methylene chloride/methanol (10:1). The fractions containing the product are freed from solvent on a rotary evaporator.

17.12 g of the title compound (57% of theory) are obtained; $R_f$: 0.345 (T/EA/$CH_3COOH$) 20:20:1.

EXAMPLE XVII

2-Cyano-N-trifluororacetyl-pyrrolidine

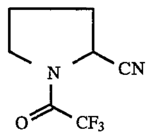

40 g (0.19 mol) of the products from Example XIII and 45 g=46 ml (0.57 mol) of pyridine are initially introduced into 300 ml of THF under protective gas. At 0° C., 48 g=32.25 ml (0.228 mol) of trifluoroacetic anhydride are added. The reaction mixture is stirred for 30 min at 0° C. and for 90 min at room temperature. The batch is then added to 1 l of 1N hydrochloric acid and extracted 3× by shaking with 200 ml of methylene chloride. The combined organic phases are extracted by shaking with 200 ml of saturated NaCl solution and dried over magnesium sulphate. The solvent is stripped off and the residue is chromatographed on silica gel 60 F254. Petroleum ether/ethyl acetate/acetic acid (1600:200:5). The fractions containing the products are concentrated. 32.4 g of the title compound (88.8% of theory) are obtained.

$R_f$: 0.57 (petroleum ether/ethyl acetate 7:3)

EXAMPLE XVIII

2-Tetrazolyl-N-trifluoroacetyl-pyrrolidine

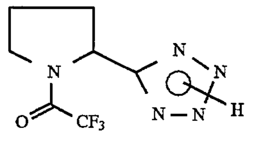

31.35 g=32.6 ml (0.26 mol) of diethylaluminiumchloride are initially introduced into 65 ml of toluene under protective gas. 29.95 g=34.04 ml (0.26 mol) of trimethylsilyl azide are added at room temperature and the mixture is stirred for 10 min at room temperature. 25 g (0.13 mol) of the product from Example XIV, dissolved in 65 ml of toluene, are added at 0° C. The reaction mixture is stirred for 30 min at 0° C., 120 min at room temperature and 60 min at 40° C. The cooled batch is treated with saturated potassium fluoride solution until evolution of gas can no longer be detected.

The reaction mixture is added to 600 ml of $H_2O$ and acidified to pH 4 and extracted 3× with 100 ml of ethyl acetate. The combined organic phases are treated with 50 ml of n-hexane. In order to remove the azides, about ⅓ of the solvent is removed by distillation over a distillation bridge without cooling. The residue is dried over magnesium sulphate and freed from solvent on a rotary evaporator.

18.54 g of the title compound (60.6% of theory) are obtained.

$R_f$: 0.4 (toluene/ethyl acetate 1:1).

EXAMPLE XIX

N-Trifluoroacetyl-2-[N-trityl-tetrazolyl]pyrrolidine

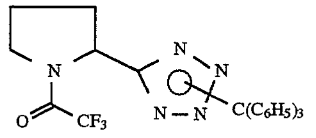

16.23 g (0.069 mol) of the product from Example XV and 10.47 g=14.35 ml (0.1035 mol) of triethylamine are initially introduced into 70 ml of methylene chloride. 19.83 g (0.069 mol) of triphenylmethyl chloride are then added. The reaction mixture is stirred for 1.5 h at room temperature, diluted with methylene chloride and extracted with pH 5 buffer solution (3×50 ml). The organic phase is dried over magnesium sulphate. The solvent is stripped off on a rotary evaporator. The residue is stirred with ether. The resulting crystals are filtered off with suction and dried.

24.65 g of the title compound (75% of theory) are obtained.

$R_f$: 0.53 (petroleum ether/ethyl acetate 7:3).

EXAMPLE XX 2-(N-Trityl-tetrazolyl)pyrrolidine

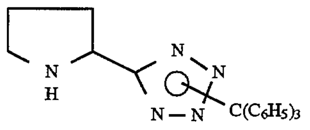

24 g (0.05 mol) of the product from Example XVI are initially introduced into 100 ml of ethanol under protective gas. 2.84 g (0.075 mol) of sodium borohydride are added in portions at 0° C. The batch is thawed and stirred at room temperature for 1 h. It is treated with 6 ml of acetic acid and the whole reaction mixture is added to 500 ml of buffer solution pH 9. The batch is extracted with 3×75 ml of methylene chloride. The combined organic phases are dried over magnesium sulphate and freed from solvent on a rotary evaporator. The residue is chromatographed on silica gel 60 F254. Petroleum ether/ethyl acetate (7:3). The corresponding fractions are concentrated and dried.

7.16 g of the title compound (37.5% of theory) are obtained.

$R_f$: 0.22 (ethyl acetate).

EXAMPLE XXI

4-Bromomethyl-3-chloro-benzenesulphonic acid-2-[trityltetrazolyl]pyrrolidinide

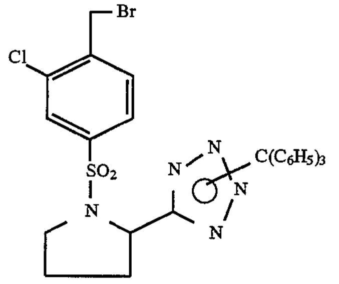

In analogy to the procedure of Example III, 6.49 g of the title compound i(95% of theory) are obtained from 3.19 g (10.5 mmol) of the compound from Example IV and 4 g (10.5 mmol) of the compound from Example XVII.
R: 0.53 (petroleum ether/ethyl acetate 7:3).

EXAMPLE XXII 4-(Bromomethyl)-3-fluorobenzenesulphochloride

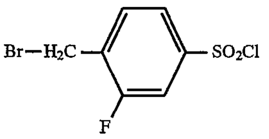

20.9 g (0.1 mol) of 3-fluoro-4-methylbenzenesulphochloride are taken up in 200 ml of carbon tetrachloride and, after addition of 19.6 g (0.11 mol) of N-bromosuccinimide and 0.3 g of dibenzoyl peroxide, the mixture is heated under reflux for 5 h. After cooling, the solids are filtered off and the filtrate is freed from solvent. Flash chromatography petroleum ether/toluene (4:1), 50 μm particle size gives 12.4 g (44% of theory) of the title compound
$R_f$: 0.42 (petroleum ether/toluene 3:1).

EXAMPLE XXIII 4-(Bromomethyl)-3-trifluoromethylbenzenesulphochloride

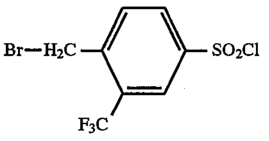

64.6 g (0.25 mol) of 3-trifluoromethyl-4-methylbenzenesulphochloride are taken up in 500 ml of carbon tetrachloride and, after addition of 44.5 g (0.25 mol) of N-bromosuccinimide and 0.4 g of ABN, the mixture is heated under reflux for 24 h. After cooling, the solids are filtered off and the filtrate is freed from solvent. Flash chromatography petroleum-ether/toluene (4:1), 50 μm particle size gives 33.9 g (40% of theory) of the title compound.
$R_f$: 0.41 (petroleum ether/toluene 3:1)

EXAMPLE XXIV (S)-4-(Bromomethyl)-3-fluorobenzenesulphonyl-N-2-(tert-butoxy-carbonyl)pyrrolidinide

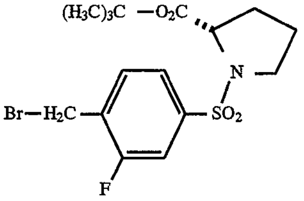

In analogy to the procedure of Example III, 12.7 g (100% of theory) of the title compound are obtained from 8.6 g (30 mmol) of the compound from Example XIX and 5.1 g (30 mmol) of S-proline tert-butyl ester.
$R_f$: 0.57 (petroleum ether/ethyl acetate 7:3).

EXAMPLE XXV (S)-4-(Bromomethy 1)-3-trif luoromethylbenzenesulphonyl-N2-(tert-butoxycarbonyl-pyrrolidinide

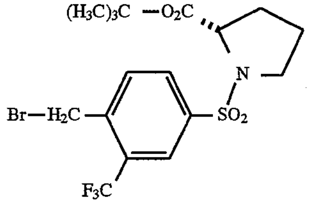

In analogy to the procedure of Example III, 23.6 g (100% of theory) of the title compound are obtained from 16.9 g (50 mmol) of the compound from Example XX and 8.6 g (50 mmol) of S-proline tert-butyl ester.
$R_f$: 0.63 (petroleum ether/ethyl acetate 7:3).

EXAMPLE XXVI (S)-4-carboxy-3-by droxybenzenesulphonyl-N-2-(tert.-butoxycarbonyl)-pyrrolidinide

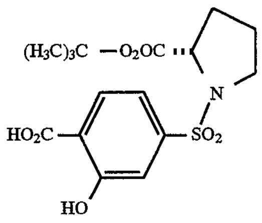

Analogously to the method of Example III, 30.0 g (81% of theory) of the title compound are obtained from 23.7 g of 4-carboxy-3-hydroxybenzenesulphochloride (100 mmol) and 17.1 g (100 mmol) of S-proline tert.-butyl ester.
$R_f$: 0.18 (acetone)

EXAMPLE XXVII (S)-4-Benzyloxycarbonyl-3-benzyloxybenzenesulphonic acid N-2-(tert.-butoxy-carbonyl)-pyrrolidinide

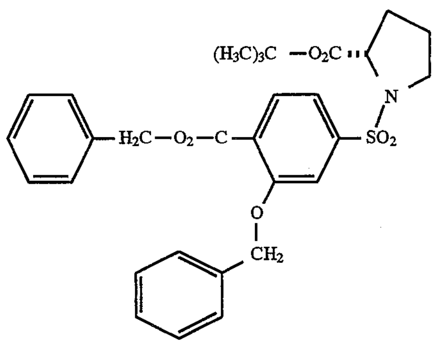

28.3 g of $K_2CO_3$ (204 mmol) and 25.7 g (150 mmol) of benzyl bromide are added to 25.3 g (68 mmol) of the compound of Example XXVI dissolved in 200 ml of DMF. The reaction mixture is stirred for a further 2 hours at 75° C. and cooled. 1 l of water is then added and the mixture is extracted with ethyl acetate (3×400 ml) and the extract washed with water (5×400 ml), dried over $MgSO_4$, filtered and all the volatile components are stripped off in vacuo. The product is purified by flash chromatography (petroleum ether/$CH_2Cl_2$ 5:1 and petroleum ether/ethyl acetate 6:1, particle size: 50μ) and then purified further by recrystallisation from 600 ml of a solvent mixture (petroleum ether/ethyl acetate 6:1). 35.5 g (95% of theory) of the title compound are obtained.

$R_f$=0.53 (petroleum ether/ethyl acetate 7:3)

EXAMPLE XVIII (S)-4-(Hydroxymethyl)-3-benzyloxybenzenesulphonic acid N-2-(tert.-butoxy-carbonyl)-pyrrolidihide

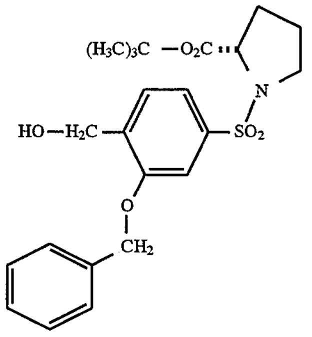

11.03 g (20 mmol) of the compound of Example XXVII are dissolved in 100 ml of diglyme and, after adding 1.51 g (40 mmol) of sodium borohydfide and 1.68 g (40 mmol) of LiCl, the mixture is stirred for 4 hours at 70° C. After cooling, 500 ml of water are added to the reaction mixture, which is then acidified with 1N HCl to a pH of 3. The mixture is extracted with ether (3×300 ml) and the extract is washed with water (6×300 ml), dried over $MgSO_4$ and the tiltrate freed from the solvent. The residue is chromatographed on silica gel 60 F 254 (petroleum ether/ethyl acetate (7:3)). The corresponding fractions are concentrated by evaporation and dried. 5.0 g (56% of theory) of the title compound are obtained.

$R_f$=0.36 (petroleum ether/ethyl acetate 7:3)

EXAMPLE XXIX (S)-4-(Bromomethyl)-3-benzyloxybenzenesulphonic acid N-2-(tert.-butoxycarbonyl)-pyrrolidinide

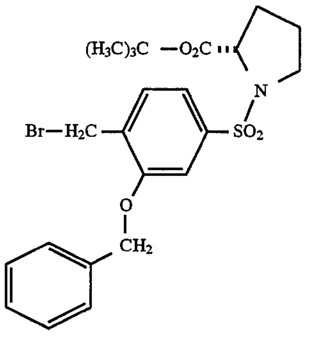

2.24 g (5 mmol) of the compound from Example XXVIII are initially introduced into 20 ml of absolute DMF under an inert gas. 2.53 g (6 mmol) of triphenylphosphine dibromide are added at 0° C. The reaction mixture is stirred for 1 hour at room temperature. 200 ml of water are added, the mixture is extracted with ethyl acetate (3×80 ml) and the extract is washed with water (5×60 ml), dried over $MgSO_4$, filtered and all the volatile components are stripped off in vacuo. The product is purified by flash chromatography ($CH_2C_{12}$, particle size: 50μ) and 2.55 g (100% of theory) of the title compound are obtained.

$R_f$=0.56 (petroleum ether/ethyl acetate 7:3)

PREPARATION EXAMPLE

Example 1 rac-4-{[2-Butyl-4-chloro-5-(3-cyclopentyl-2-methoxycarbonylpropenyl)imidazolyl]methyl}-3-chlorobenzene-sulphonyl-N-(2-tert-butoxycarbonyl) piperidinide

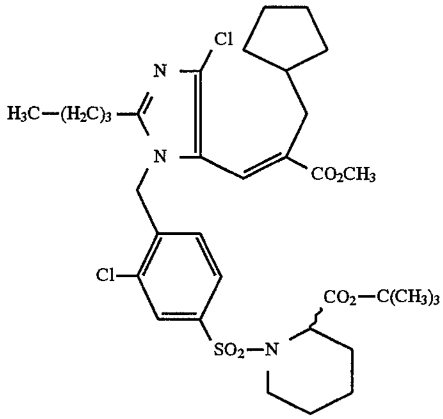

375 mg (2.4 mmol) of methyl 3-cyclopentylpropanecarboxylate are added at -78° C. to a solution of 2.56 mmol of lithium diisopropylamide [prepared in situ from 357 μl (2.56 mmol) of N,N-diisopropylamine in 6.6 ml of THF and 1.5 ml (2.88 mmol) of a 15% strength solution of n-butyllithium in hexane] in 8.1 ml of solvent and the mixture is stirred for 30 min. 900 mg (1.6 mmol) of the compound from Example XIV dissolved in 6.6 ml of THF are then added at this temperature and the mixture is then stirred for 1 h at 0° C. A solution of 163 μl (1.75 mmol) of acetic anhydride and 444 μl (3.19 mmol) of triethylamine in 0.5 ml of dichloromethane is added at 0° C. to the resulting reaction mixture and it is stirred at 20° C. for 2.5 h. The reaction mixture is then treated with 20 ml of $H_2O$ and extracted twice with 30 ml of dichloromethane each time. The combined organic phases are extracted by shaking with saturated $NaHCO_3$ solution (1×30 ml) and saturated NaCl solution (2×30 ml), dried over $MgSO_4$ and freed from the solvent. 1.35 g of a crude product are obtained, which is further reacted without further purification. The crude product is taken up in 17 ml of toluene, treated with 666 mg (4.4 mmol) of DBU and stirred for 8 h at 95° C. After cooling, the solution is diluted with 400 ml of toluene and extracted by shaking with 1N HCl (2×100 ml) and then with saturated NaCl (1×100 ml), and the organic phase is dried over $MgSO_4$ and freed from the solvent. The crude product (1.21 g) is purified by chromatography on silica gel (50 μm, dichloromethane/ethyl acetate 20:1→15:1) 341 mg (29.5% of theory) are obtained.

$R_f$=0.80 (d)

Example 2 rac-4-{[2-Butyl-4-chloro-5-(3-cyclopentyl-2-methoxycar-bonylprop-1-enyl)imidazolyl]methyl}-3-chlorobenzene-sulphonyl-N-(2-carboxy) piperidinide

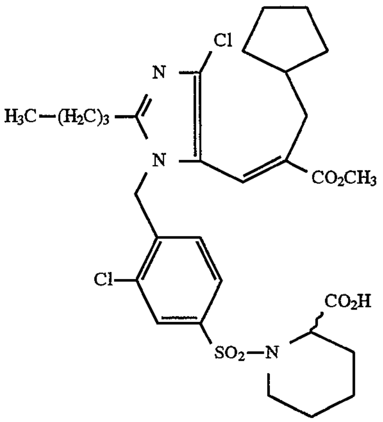

270 mg (0.41 mmol) of the compound from Example 1 are dissolved in 5ml of dichloromethane and treated at 0° C. with 1 ml of trifluoroacetic acid. The mixture is stirred at 20° C. for 5 h, all the volatiles are stripped off in vacuo and 322 mg of a crude product are obtained, which is taken up in 200 ml of ether, washed with $H_2O$ (4×50 ml) and dried ($MgSO_4$). After stripping off the solvent, 229 mg (87%; 25.9% over all steps) of the title compound are obtained.

$R_f$=0.66 (f)

EXAMPLE 3 rac-4-{[2-Butyl-4-chloro-5-(3-cyclopentyl-2-carboxyprop1-enyl) imidazolyl]methyl}-3-chlorobenzenesulphonyl-N-(2carboxy)piperidinide

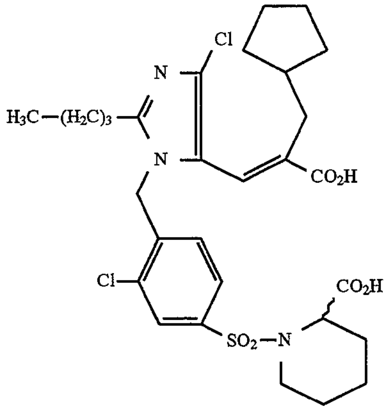

160 mg (0.25 mmol) of the compound from Example 2 are dissolved in a mixture of 1 ml of THF, 1 ml of $H_2O$ and 50 µl of methanol and treated with 64 mg (1.5 mmol) of lithium hydroxide. The mixture is stirred at 20° C. for 10 h, all the volatiles are stripped off and the residue is taken up in 20 ml of $H_2O$ and 20 ml of ethyl acetate. The solution is acidified with acetic acid (pH=3), the phases are separated and the aqueous phase is extracted once more with 40 ml of ethyl acetate. The combined organic phases are washed eight times with 20 ml of $H_2O$ each time, then once with saturated NaCl solution and dried over $MgSO_4$. 154 mg (99%, 25.5% over all steps) of the title compound are obtained.

The compounds shown in Tables 1 and 2 were prepared in analogy to the procedures for the compounds of Examples 1–3.

TABLE 1

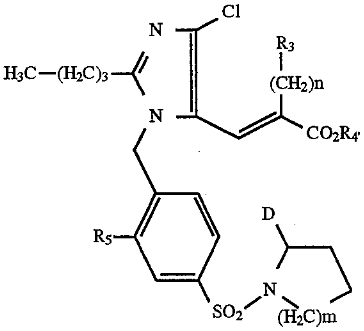

| Ex. No. | n | $R^3$ | $R^{4'}$ | $R^5$ | m | D | Config. | $R_f$* | Yield [%] |
|---|---|---|---|---|---|---|---|---|---|
| 4 | 0 | H | $-C_2H_5$ | H | 2 | H | — | 0.74[a] | 30 |
| 5 | 0 | H | $-C_2H_5$ | H | 1 | H | — | 0.71[a] | 54.7 |
| 6 | 0 | H | H | H | 1 | H | — | 0.35[a] | 36.5 |
| 7 | 1 | 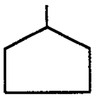 | $-CH_3$ | H | 2 | H | — | 0.63[c] | 18.5 |
| 8 | 1 | 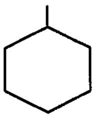 | $-CH_3$ | H | 2 | H | — | 0.54[e] | 10.6 |

TABLE 1-continued
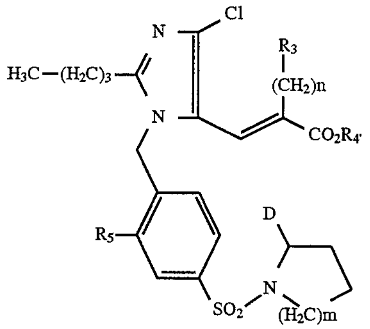
| Ex. No. | n | $R^3$ | $R^{4'}$ | $R^5$ | m | D | Config. | $R_f$* | Yield [%] |
|---|---|---|---|---|---|---|---|---|---|
| 9 | 1 | 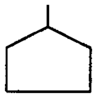 | H | H | 2 | H | — | 0.51[b] | 13.6 |
| 10 | 1 | 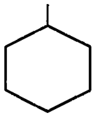 | H | H | 2 | H | — | 0.56[b] | 2.0 |
| 11 | 1 | 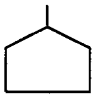 | $-CH_3$ | H | 2 | $CO_2C(CH_3)_3$ | rac | 0.8[d] | 21.5 |
| 12 | 1 | 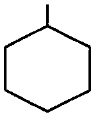 | $-CH_3$ | H | 2 | $CO_2C(CH_3)_3$ | rac | 0.75[d] | 29.2 |
| 13 | 1 | 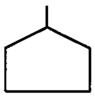 | $-CH_3$ | H | 2 | $CO_2H$ | — | 0.11[d] | 21.5 |
| 14 | 1 | 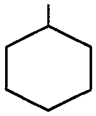 | $-CH_3$ | Cl | 1 | $-CO_2C(CH_3)_3$ | S | 0.78[d] | 5.5 |
| 15 | 1 | 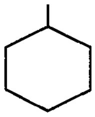 | $-CH_3$ | H | 2 | $-CO_2H$ | rac | 0.45[b] | 29.2 |
| 16 | 1 | 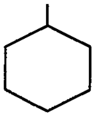 | $-CH_3$ | H | 1 | $-CO_2C(CH_3)_3$ | S | 0.74[d] | 26.4 |
| 17 | 1 | 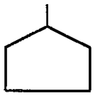 | $-CH_3$ | Cl | 2 | $-CO_2C(CH_3)_3$ | rac | 0.80[d] | 29.5 |
| 18 | 1 | 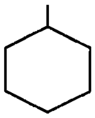 | $-CH_3$ | H | 1 | $-CO_2H$ | S | 0.46[f] | 25.0 |

TABLE 1-continued
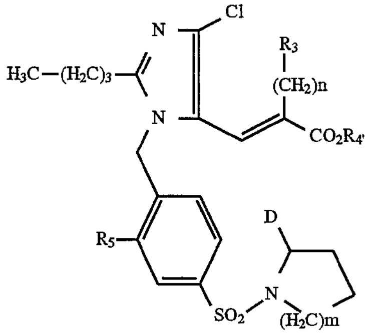
| Ex. No. | n | $R^3$ | $R^{4'}$ | $R^5$ | m | D | Config. | $R_f$* | Yield [%] |
|---|---|---|---|---|---|---|---|---|---|
| 19 | 1 | 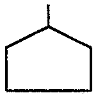 | H | H | 1 | $-CO_2H$ | S | $0.26^f$ | 6.3 |
| 20 | 1 | 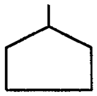 | H | Cl | 2 | $-CO_2H$ | rac | $0.63^f$ | 25.5 |
| 21 | 1 | 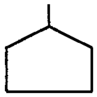 | $-CH_3$ | Cl | 2 | $-CO_2H$ | rac | $0.66^f$ | 25.9 |
| 22 | 1 | 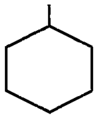 | H | H | 2 | $-CO_2H$ | rac | $0.73^b$ | 19.9 |
| 23 | 1 | 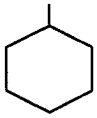 | H | H | 1 | $-CO_2H$ | S | $0.30^f$ | 24.0 |
| 24 | 1 | 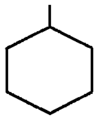 | H | Cl | 1 | $-CO_2H$ | S | $0/45^f$ | 18.9 |
| 25 | 1 | 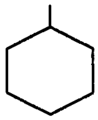 | $-CH_3$ | Cl | 3 | $-CO_2H$ | S | | |

TABLE 2

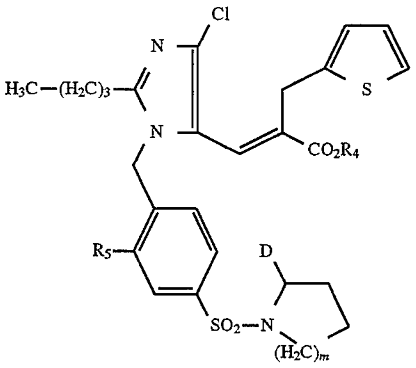

| Ex. No. | $R^{4'}$ | $R^5$ | m | D | Config. | $R_f$* | Yield [%] |
|---|---|---|---|---|---|---|---|
| 26 | $-CH_3$ | H | 1 | H | — | 0.18[c] | 22.7 |
| 27 | $-CH_3$ | H | 2 | H | — | 0.46[d] | 25.5 |
| 28 | H | H | 1 | H | — | 0.38[b] | 7.3 |
| 29 | H | H | 2 | H | — | 0.47[b] | 18.4 |
| 30 | $-CH_3$ | H | 2 | $-CO_2C(CH_3)_3$ | rac | 0.68[d] | 16.5 |
| 31 | $-CH_3$ | H | 2 | $-CO_2H$ | rac | 0.11[d] | 10.8 |
| 32 | H | Cl | 2 | $-CO_2H$ | rac | 0.62[f] | 16.5 |
| 33 | H | H | 1 | $-CO_2H$ | S | 0.24[f] | 4.4 |
| 34 | $-CH_3$ | Cl | 1 | $-CO_2H$ | S | | |
| 35 | H | Cl | 1 | $-CO_2H$ | S | | |

General Procedure for the Preparation of the Alkali Metal Salts

One equivalent of the acid is dissolved in a dioxane/water mixture, treated with one equivalent of a, 1N solution of the appropriate alkali, frozen and then lyophilised.

The compounds shown in Table 3 are prepared in analogy to the abovementioned methods:

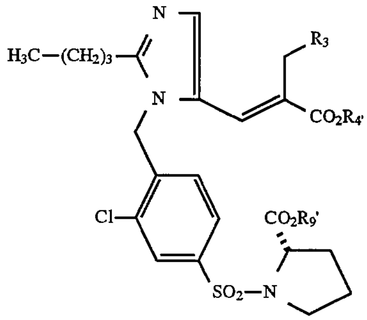

| Ex. No. | $R^3$ | $R^{4'}$ | $R^9$ | $R_f$* | Yield [% of th.] |
|---|---|---|---|---|---|
| 36 | $-C_2H_5$ | $CH_3$ | H | 0.25[a] | 84 |
| 37 | $-C_2H_5$ | $CH_3$ | Na | n.a. | 99.7 |
| 38 | $-C_2H_5$ | H | H | 0.17[a] | 71 |
| 39 | $-C_2H_5$ | Na | Na | n.a. | 100 |
| 40 | $-CH(CH_3)_2$ | $-C_2H_5$ | H | 0.29[a] | 100 |
| 41 | $-CH(CH_3)_2$ | $-C_2H_5$ | Na | n.a. | 99.9 |
| 42 | $-CH(CH_3)_2$ | H | H | 0.18[a] | 76 |
| 43 | $-CH(CH_3)_2$ | Na | Na | n.a. | 99.9 |
| 44 | 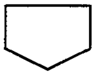 | $CH_3$ | H | 0.3[a] | 99.6 |

-continued

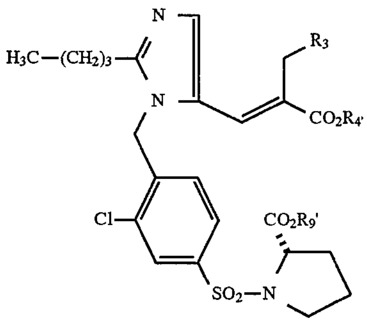

| Ex. No. | $R^3$ | $R^{4'}$ | $R^9$ | $R_f$* | Yield [% of th.] |
|---|---|---|---|---|---|
| 45 | 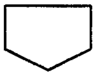 | $CH_3$ | Na | n.a. | 99.8 |
| 46 | 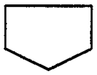 | H | H | 0.21[a] | 94 |
| 47 | 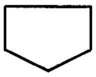 | Na | Na | n.a. | 100 |
| 48 | 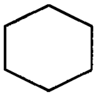 | $CH_3$ | H | 0.2[a] | 100 |
| 49 | 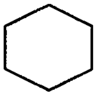 | $CH_3$ | Na | n.a. | 100 |
| 50 | 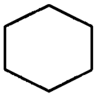 | H | H | 0.16[a] | 34 |
| 51 | 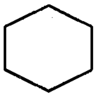 | Na | Na | n.a. | 100 |
| 52 | 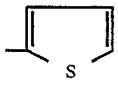 | $CH_3$ | H | 0.23[a] | 85 |
| 53 | 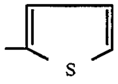 | $CH_3$ | Na | n.a. | 100 |
| 54 | 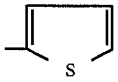 | H | H | 0.12[a] | 81 |
| 55 | 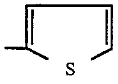 | Na | Na | n.a. | 99.9 |
| 56 | 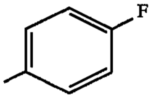 | $CH_3$ | H | 0.31[a] | 95 |

-continued

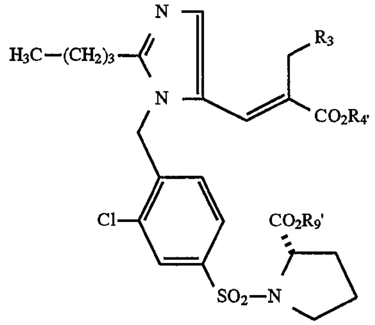

| Ex. No. | $R^3$ | $R^{4'}$ | $R^9$ | $R_f$* | Yield [% of th.] |
|---|---|---|---|---|---|
| 57 | 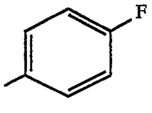 | $CH_3$ | Na | n.a. | 99.8 |
| 58 | 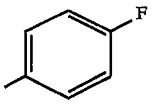 | H | H | 0.19[a] | 98 |
| 59 | 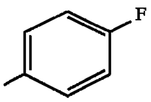 | Na | Na | n.a. | 99.8 |

[a]Toluene/methanol/glacial acetic acid = 35:5:1

We claim:

1. An aldehyde of the formula

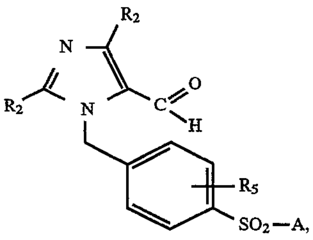

(II)

in which $R^1$ represents straight-chain or branched alkyl or alkenyl each having up to 8 carbon atoms, each of which is optionally substituted by cycloalkyl having 3 to 6 carbon atoms, or represents cycloalkyl having 3 to 8 carbon atoms, $R^2$ represents hydrogen, halogen or straight-chain or branched perfluoroalkyl having up to 8 carbon atoms, $R^5$ represents hydrogen, halogen or straight-chain or branched alkyl having up to 8 carbon atoms, or represents straight-chain or branched perfluoroalkyl having up to 6 carbon atoms, or represents a group of the formula —OX, in which X denotes hydrogen, benzyl, a hydroxyl protective group selected from the group consisting of benzyloxycarbonyl, methanesulphonyl, toluenesulphonyl, 2-nitrobenzyl, 4-nitrobenzyl, 2-nitrobenzyloxycarbonyl, 4-nitrobenzyloxycarbonyl, tert-butoxycarbonYl, allyloxycarbonyl, 4-methoxycarbonyl, acetyl, trichloroacetyl, 2,2,2-trichloroethoxycarbonyl, 2,4-dimethoxybenzyloxycarbonyl, 2-(methylthiomethoxy) ethoxycarbonyl, benzoyl, 4-methylbenzoyl, 4-nitrobenzoyl, 4-fluorobenzoyl, 4-chlorobenzoyl or 4-methoxybenzoyl or denotes straight-chain or branched alkyi having up to 8 carbon atoms A represents pyrrolidinyl which is optionally substituted up to 2 times by identical or different perfluoroalkyl having up to 5 carbon atoms or a salt thereof.

2. An aldehyde according to claim 1, in which represents straight-chain or branched alkyl or alkenyl each having up to 6 carbon-atoms, each of which is optionally substituted by cyclopropyl, cyclobutyl, cyclopentyl or cyclohexyl, represents cyclopropyl, cyclopentyl or cyelohexyl, $R^2$ represents hydrogen, fluorine, chlorine, bromine or straight chain or branched perfluoroalkyl having up to 6 carbon atoms, $R_5$ represents hydrogen, fluorine, chlorine, bromine, straight-chain or branched alkyl having up to 6 carbon atoms, or represents straight-chain or branched perfluoroalkyl having up to 4 carbon atoms, or represents a group of the formula —OX, in which X denotes hydrogen, benzyl, acetyl or straight-chain or branched alkyl with up to 6 carbon atoms A represents pyrrolidinyl which is optionally substituted by trifluoromethyl or a salt thereof.

3. An aldehyde according to claim 1, in which $R^1$ represents straight-chain or branched alkyl or alkenyl each having up to 4 carbon atoms, or cyclopropyl, $R^2$ represents hydrogen, fluorine, chlorine, or straight-chain or branched perfluoroalkyl having up to 4 carbon atoms, $R^5$ represents hydrogen, fluorine, chlorine or straight-chain or branched alkyl having up to 4 carbon atoms, or represents straight-chain or branched perfluoroalkyl having up to 3 carbon atoms, or represents a group of the formula —OX, in which X denotes hydrogen, benzyl, acetyl or straight-chain or branched alkyl with up to 6 carbon atoms, A represents pyrrolidinyl bonded via the nitrogen atom, which is optionally substituted by trifluoromethyl or a salt thereof.

* * * * *

UNITED STATES PATENT AND TRADEMARK OFFICE

CERTIFICATE OF CORRECTION

PATENT NO. : 5,627,285 Page 1 of 2

DATED : May 6, 1997

INVENTOR(S) : Hanko, et al.

It is certified that error appears in the above-indentified patent and that said Letters Patent is hereby corrected as shown below:

Col. 33, lines 35-43 Delete "

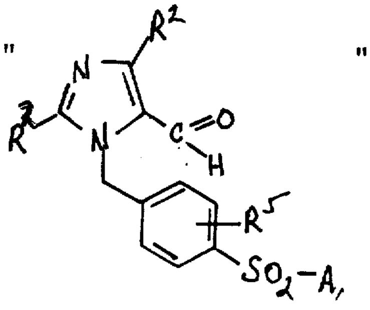

" and substitute --

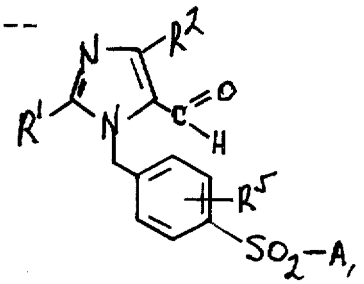

--

Col. 34, line 18 Before " represents " insert -- $R^1$ --

UNITED STATES PATENT AND TRADEMARK OFFICE

CERTIFICATE OF CORRECTION

PATENT NO. : 5,627,285

DATED : May 6, 1997

INVENTOR(S) : Hanko, et al.

It is certified that error appears in the above-indentified patent and that said Letters Patent is hereby corrected as shown below:

Col. 34, line 22 Delete " cyelohexyl " and substitute -- cyclohexyl --

Signed and Sealed this

Ninth Day of December, 1997

Attest:

BRUCE LEHMAN

Attesting Officer

*Commissioner of Patents and Trademarks*